US005667485A

United States Patent [19]
Lindsay

[11] Patent Number: 5,667,485
[45] Date of Patent: Sep. 16, 1997

[54] BLOOD RESERVOIR WITH VISIBLE INLET TUBE

[75] Inventor: Erin J. Lindsay, Manchester, Mich.

[73] Assignee: Minnesota Mining and Manufacturing Company, St. Paul, Minn.

[21] Appl. No.: 431,886

[22] Filed: May 1, 1995

[51] Int. Cl.$^6$ ................................ A61M 37/00
[52] U.S. Cl. ................................ 604/4; 137/615
[58] Field of Search ................... 604/4; 137/615

[56] References Cited

U.S. PATENT DOCUMENTS

| | | | |
|---|---|---|---|
| 3,891,416 | 6/1975 | Leonard et al. | 55/178 |
| 3,993,461 | 11/1976 | Leonard et al. | 55/178 |
| 4,183,961 | 1/1980 | Curtis | 424/366 |
| 4,208,193 | 6/1980 | Munsch et al. | 55/36 |
| 4,243,531 | 1/1981 | Crockett et al. | 210/188 |
| 4,435,170 | 3/1984 | Laszczower | 604/4 |

(List continued on next page.)

FOREIGN PATENT DOCUMENTS

| | | | |
|---|---|---|---|
| 0 207 304 | 1/1987 | European Pat. Off. | A61M 1/00 |
| 0 313 107 | 4/1989 | European Pat. Off. | A61M 1/00 |
| 0 312 101 | 4/1989 | European Pat. Off. | A61M 5/14 |
| 777243 | 2/1935 | France . | |

OTHER PUBLICATIONS

Brochure entitled "Bard® William Harvey® HF-5701 Membrance Oxygenator—Directions for Use"; Bard Cardiopulmonary Division of C.R. Bard, Inc.; No. R3355/6-92/B (apparently dated Jun. 1992).

Brochure entitled "Making the best even better!"; Cobe Laboratories, Inc.; Form No. 421-200-027 (apparently 1985).

Brochure entitled "Hemodynamic Duo"; Gish Biomedical, Inc.; (apparently 1987).

(List continued on next page.)

*Primary Examiner*—Randy C. Shay
*Attorney, Agent, or Firm*—Gary L. Griswold; Walter N. Kirn; Stephen W. Bauer

[57] ABSTRACT

A blood reservoir adapted for use in an extracorporeal circulatory support circuit. The blood reservoir includes a visible inlet tube that extends vertically outside the housing of the reservoir to allow visual observation of venous blood flowing in the inlet tube. The inlet tube is releasably held generally adjacent the top of the housing to allow the reservoir to be converted between top and bottom mounted venous blood inlets with a single inlet, as well as permitting the inlet tube to be moved to a position extending downwardly from the reservoir to allow draining the reservoir through the inlet tube after surgery. A generally funnel-shaped inlet portion may be provided in the inlet adjacent the chamber to decelerate blood before it enters the chamber, and a diverter cone may be provided over a venous inlet portion to divert the incoming blood.

19 Claims, 5 Drawing Sheets

U.S. PATENT DOCUMENTS

| | | | |
|---|---|---|---|
| 4,451,562 | 5/1984 | Elgas et al. | 435/2 |
| 4,469,659 | 9/1984 | Carson et al. | 422/46 |
| 4,642,089 | 2/1987 | Zupkas et al. | 604/4 |
| 4,656,004 | 4/1987 | Stewart | 422/46 |
| 4,664,682 | 5/1987 | Monzen | 55/178 |
| 4,705,497 | 11/1987 | Shitaokoshi et al. | 604/4 |
| 4,737,139 | 4/1988 | Zupkas et al. | 604/4 |
| 4,818,490 | 4/1989 | Carson et al. | 422/46 |
| 4,846,800 | 7/1989 | Ouriel et al. | 604/4 |
| 4,909,780 | 3/1990 | Ouriel et al. | 604/4 |
| 4,923,438 | 5/1990 | Vasconcellos et al. | 604/4 |
| 4,936,759 | 6/1990 | Clausen et al. | 417/423 |
| 5,039,430 | 8/1991 | Corey, Jr. | 210/806 |
| 5,061,236 | 10/1991 | Sutherland et al. | 604/4 |
| 5,078,677 | 1/1992 | Gentelia et al. | 604/4 |
| 5,087,250 | 2/1992 | Lichte et al. | 604/321 |
| 5,127,900 | 7/1992 | Schickling et al. | 604/4 |
| 5,149,318 | 9/1992 | Lindsay | 604/4 |
| 5,152,964 | 10/1992 | Leonard | 422/48 |
| 5,158,533 | 10/1992 | Strauss et al. | 604/4 |
| 5,254,080 | 10/1993 | Lindsay | 604/4 |
| 5,270,005 | 12/1993 | Raible | 422/46 |
| 5,282,783 | 2/1994 | Lindsay | 604/4 |
| 5,304,164 | 4/1994 | Lindsay | 604/403 |
| 5,328,461 | 7/1994 | Utterberg | 604/80 |
| 5,399,156 | 3/1995 | Lindsay | 604/4 |
| 5,403,273 | 4/1995 | Lindsay | 604/4 |

OTHER PUBLICATIONS

"Instructions for Use" Baxter Bentley® Univox™IC Open Membrane Oxygenation System —Single Use Only —Do Not Resterilize; Baxter Healthcare Corporation; Sep. 19, 1990.

Brochure entitled "Sarns Filtered Venous Reservoir"; 3M Health Care; 1991; Form No. 78-8067-3371-9.

Brochure entitled "When you bring efficiency to the surface . . . you can lower the prime."; 3M Health Care; 1990; Form No. 16088004 Rev. B.

Brochure entitled "SMO/INF Sarns Infant Membrane Oxygenator"; 3M 1990; Form No. 78-8066-9351-7.

Brochure entitled "SMO/IR Sarns Membrane Oxygenator with Integral Reservoir"; 3M 1990; Form No. 78-8066-9350-9.

Brochure entitled "SMO/ICR Sarns Membrane Oxygenator with Integral Cardiotomy Reservoir"; 3M 1990; Form No. 78-8066-9349-1.

Brochure entitled "Sarns™ SMO/ICR Membrance Oxygenator with Integral Cardiotomy Reservoir —Instructions"; 3M; Sep. 1990; Form No. 34-9998-9114-5 R/C.

Brochure entitled "COBE® CML Ultra—When Priming Volume really counts . . . "; Cobe Laboratories, Inc.; 1989, Form No. 421-200-051

Brochure entitled "Cobe® Membrane Lung (CML) Blood Oxygenator —Performance Characteristics"; Cobe Laboratories, Inc.; 1983.

Brochure entitled "Cobe CML—Blood Oxygenator with Integral Filter"; Cobe Laboratories, Inc., Oct. 1989; Form No. 434303-101 Rev. A.

Brochure entitled "Now everyone can breathe easier Cobe CML", Cobe Laboratories, Inc.; 1983.

Brochure entitled "New Cobe VPCML—One Size Fits Small"; Cobe Laboratories, Inc.; 1984.

Brochure entitled "HSVRF—Hardshell Venous Reservoir with Integral Cardiotomy Filter—Instructions for Use"; Shiley Incorporated; 1987; Form No. DP22-2025-001 (Nov. 1987).

E Iatridis et al.; "Range of usage for the Variable Prime Cobe Membrane Lung (VPCML)", Perfusion, 1986. 1:277–279.

J.R. Crockett et al.; "The Variable Prime Cobe Membrane Lung: first impressions"; Perfusion 1987. 2:205–12.

A. Iatridis; "Laboratory Evaluation of the Variable Prime Cobe Membrane Lung"; Proceedings of the American Academy of Cardiovascular Perfusion, vol. 6, Jan. 1985. .

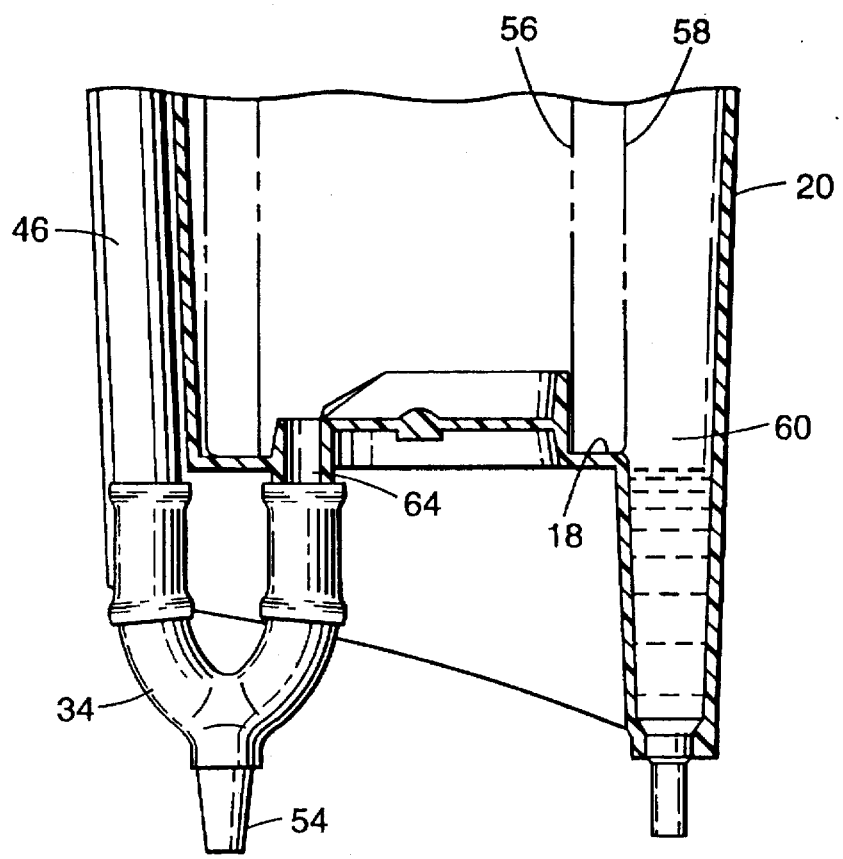
*Fig. 2*
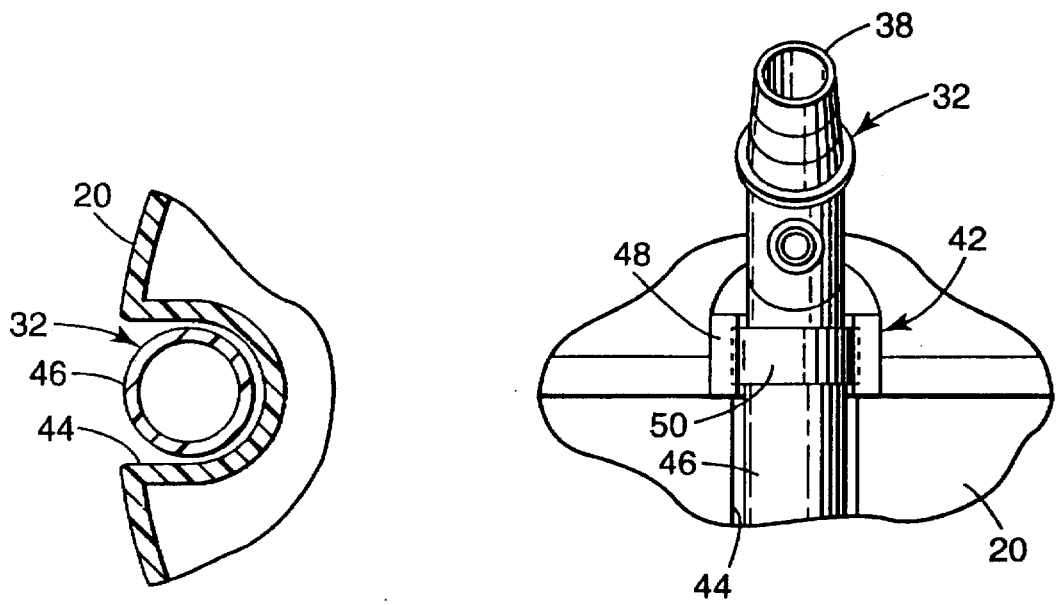
*Fig. 3*  *Fig. 4*

BLOOD RESERVOIR WITH VISIBLE INLET TUBE

This invention relates to a blood reservoir, and more particularly to a blood reservoir of the type used in an extracorporeal circulatory support circuit.

BACKGROUND OF THE INVENTION

Rigid blood reservoirs have been used as part of an extracorporeal circulatory support circuit for many years in order to hold venous blood drained from a patient during heart bypass surgery and/or to hold blood scavanged from the surgical field during such surgery. Examples of rigid blood reservoirs are shown in coassigned U.S. Pat. Nos. 5,149,318; 5,152,964; 5,254,080; 5,282,783; 5,304,164 and 5,403,273. Rigid blood reservoirs of this type have been available under the trade designation "SARNS™" venous reservoir and integral venous/cardiotomy reservoir from Minnesota Mining and Manufacturing Company, St. Paul, Minn.

For purposes of the background of this invention, many prior rigid blood reservoirs came in two types: (1) reservoirs having top mounted venous blood inlets, and (2) reservoirs having bottom mounted venous inlets. A top inlet reservoir typically includes a tubing connector mounted on the top of the reservoir, with an internal tube extending downwardly from the connector into the chamber defined by the reservoir. A bottom inlet reservoir includes a tubing connector mounted on the bottom of the reservoir, with blood entering the reservoir through the floor of the blood chamber. The blood reservoirs available under the trade designation "SARNS™" have included both bottom and top mounted venous blood inlets. See, e.g., U.S. Pat. Nos. 5,282,783 and 5,403,273.

There is a need for a blood reservoir in which a single venous blood inlet can function as both a bottom and top type inlet. This would allow one connection to be made to the venous inlet, while permitting the blood reservoir to be converted during use between the top and bottom venous inlet types. For example, the reservoir could be used as top inlet type during surgery, and converted to a bottom inlet type after surgery to facilitate draining the reservoir through the venous inlet. In addition, such a reservoir inlet would provide a visible inlet drop tube so that the perfusionist can observe the blood flowing in the inlet, and have the visual reassurance that the inlet tube will remain primed.

Generally, the reservoir of the invention comprises a housing having top, bottom and side walls defining a chamber inside the housing for holding fluid. An outlet is provided adjacent the bottom of the housing for draining fluid from the bottom of the chamber. The outlet has a connector for connecting tubing in fluid communication with the outlet. A novel inlet tube is connected to the housing outside the housing for supplying fluid to the chamber. The inlet tube comprises an elongate tube having a resiliently-flexible portion connecting the inlet tube in fluid communication with the chamber at or adjacent the bottom of the chamber and a free end opposite the resiliently-flexible portion. The free end of the inlet tube has a connector for connecting tubing in fluid communication with the inlet tube. A holding means is provided for releasably holding the inlet tube in a first position, in which the inlet tube is held in a generally vertical orientation generally adjacent the side wall of the housing. The inlet tube has a length that brings the connector of the inlet tube into generally close proximity with the top of the housing when the holding means holds the inlet tube in its first position. The blood reservoir can be converted between top and bottom inlet configurations by moving the inlet tube between its first position and other positions in which the inlet tube is not held by the holding means.

Preferably, the side wall of the housing has a generally vertically extending channel formed therein for releasably receiving the inlet tube. For example, the side wall has a channel-forming portion having a generally U-shaped horizontal cross section.

Most preferably, the inlet tube is formed of generally transparent material, allowing visual observation of blood flowing through inlet tube.

Also, preferably, the holding means comprises means for releasably grasping the inlet tube generally adjacent the top of the housing. For example, the means for releasably grasping may comprise a resilient clip.

Preferably, the connector at the free end of the inlet tube includes a swivel-type connection means.

Also, preferably, the inlet tube comprises a main portion extending between the resiliently-flexible portion and the connector, the main portion of the inlet tube being formed of generally rigid material.

Most preferably, the inlet tube may be moved between its first position to a second position, in which the connector of the inlet tube is positioned at a lower elevation than the bottom of the reservoir to drain the reservoir through the inlet, and to a third position, intermediate the first and second positions, in which the inlet tube extends upwardly at an angle to the vertical.

In another aspect of the invention, the blood reservoir, which may or may not include the visible inlet tube, generally comprises a housing having top, bottom and side walls defining a chamber inside the housing for holding fluid. A blood defoaming medium is provided within the chamber, with the blood defoaming medium defining an antechamber holding blood before it passes through the blood defoaming medium, and a blood storage portion of the chamber outside the blood defoaming medium for storing defoamed blood. An outlet is provided adjacent the bottom of the housing for draining fluid from the bottom of blood storage portion of the chamber. The outlet has a connector for connecting tubing in fluid communication with the outlet. An inlet is provided adjacent the bottom of the housing for supplying fluid to the chamber. The inlet has a connector for connecting tubing in fluid communication with the inlet, and an inlet opening through the bottom wall of the reservoir into the antechamber. A novel diverter cone is held concentrically over the inlet opening, and tapers downwardly in the direction toward the inlet opening. The diverter cone diverts blood entering the chamber via the inlet generally radially outwardly.

Preferably, the inlet includes a generally funnel-shaped inlet portion adjacent the inlet opening to decelerate venous blood flowing in the inlet potion before the blood enters the antechamber of the reservoir.

Also, preferably, a mounting vane extends upwardly from the bottom wall of the housing into the antechamber for holding the diverter cone in concentric position over the inlet opening. The mounting vane is most preferably radially aligned with respect to the diverter cone.

Further details of the invention are defined in the features of the claims. These and other features and advantages will be pointed out hereinafter.

BRIEF DESCRIPTION OF THE DRAWINGS

The invention will be further described with reference to the drawing wherein corresponding reference characters indicate corresponding parts throughout the several views of the drawing, and wherein:

FIG. 2 is a vertical cross-sectional view of the reservoir of FIG. 1;

FIG. 3 is a cross-sectional view substantially along line 3—3 of FIG. 1, illustrating a channel formed in the side wall of the reservoir's housing;

FIG. 4 is a cross-sectional view substantially along line 4—4 of FIG. 1, illustrating one embodiment of a holding means for holding the inlet tube;

DETAILED DESCRIPTION OF PREFERRED EMBODIMENTS

Figure 1:
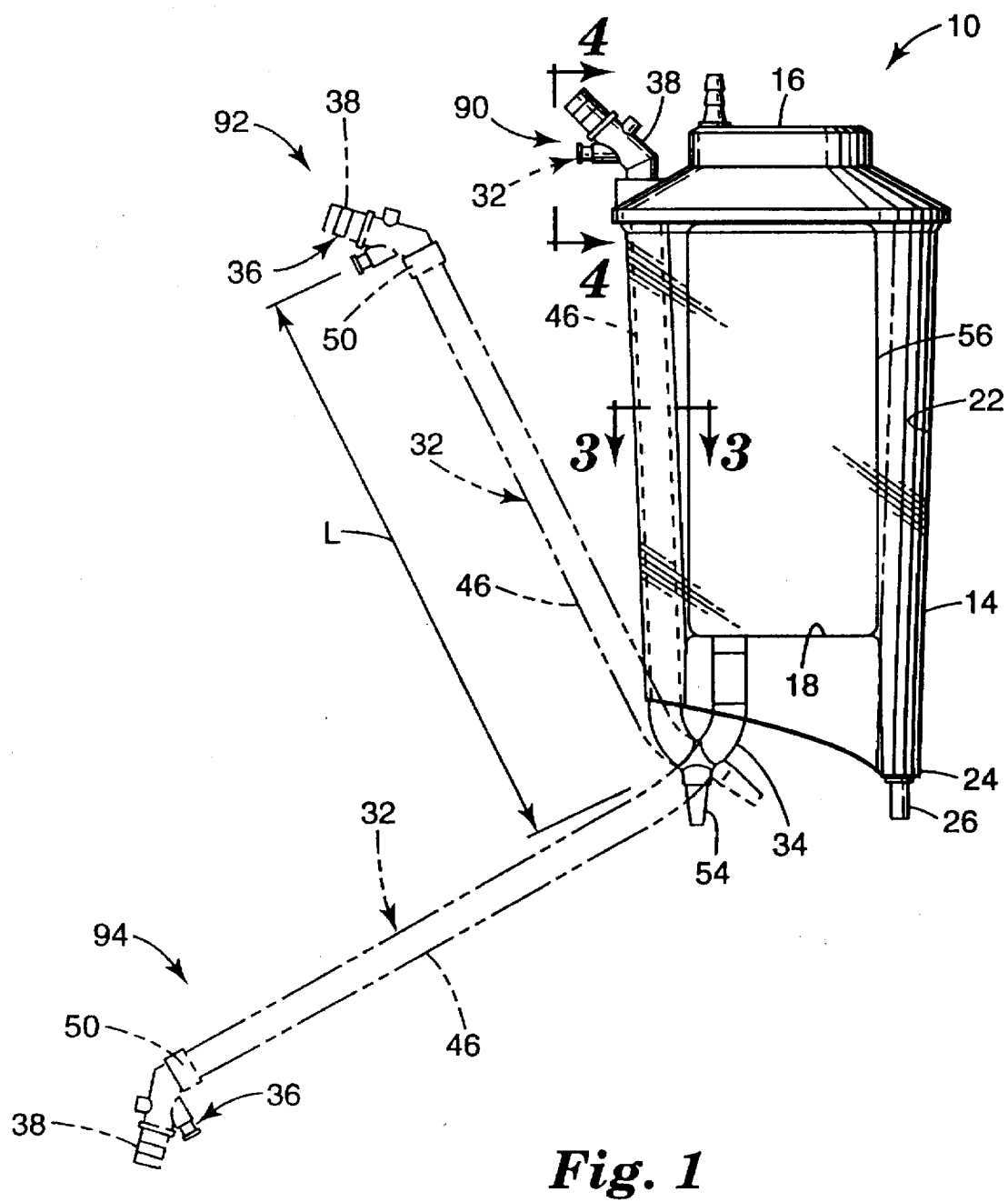
FIG. 1 is a side elevational view of the reservoir of the invention, illustrating the inlet tube in its first position and, in phantom, the inlet tube in its second and third positions.

Now referring to the drawing, a reservoir of the invention is indicated in its entirety by the reference numeral 10. The reservoir 10 may be a venous blood reservoir or integral venous/cardiotomy blood reservoir of the type used in an extracorporeal circulatory support circuit 66 (FIG. 6) during heart bypass surgery.

The reservoir 10 generally comprises a housing 14 having top, bottom and side walls 16, 18 and 20, respectively, defining an internal chamber 22 for holding blood. An outlet 24 is provided adjacent the bottom 18 of the housing 14 for draining fluid from the bottom of the chamber 22. The outlet 24 has a connector 26 for connecting tubing 28 in fluid communication with the outlet 24. The tubing 28 leads to a perfusion pump 30 (FIG. 6), which may be a peristaltic roller type pump or a centrifugal blood pump.

A novel inlet tube 32 is connected to the housing 14 outside the housing 14 for supplying fluid to the chamber 22. The inlet tube 32 comprises an elongate tube (also 32) having a resiliently-flexible portion 34 connecting the inlet tube 32 in fluid communication with the chamber 22 at or adjacent the bottom of the chamber 22 and a free end 36 opposite the resiliently-flexible portion 36. The free end 36 of the inlet tube 32 has a connector 38 for connecting tubing 40 in fluid communication with the inlet tube 32. A suitable holding means 42 (FIG. 4) is provided for releasably holding the inlet tube 32 in a first position 90 (FIG. 1 ), in which the inlet tube 32 is held in a generally vertical orientation generally adjacent the side wall 20 of the housing 14. The inlet tube 32 has a length "L" that brings the connector 38 of the inlet tube 32 into generally close proximity with the top 16 of the housing 14 when the holding means 42 holds the inlet tube 32 in its first position. The blood reservoir 10 can be converted between top and bottom inlet configurations by moving the inlet tube 32 between its first position and other positions (e.g., 92 and 94 shown in phantom) in which the inlet tube 32 is not held by the holding means 42.

Preferably, the side wall 20 of the housing 14 has a generally vertically extending channel 44 (FIG. 3) formed therein for releasably receiving the generally rigid portion 46 of the inlet tube 32. The channel-forming portion (also 44) of the side wall 20 has a generally U-shaped generally horizontal cross section (FIG. 3) that is larger than the cross sectional diameter of the rigid portion 46 of the inlet tube 32. The channel 44 is most preferably sufficiently deep to completely receive the rigid portion 46 of the inlet tube 32 without the inlet tube 32 projecting past the outer periphery of the side wall 20.

Also, preferably, the holding means 42 comprises means (also 42) for releasably grasping the inlet tube 32 generally adjacent the top 16 of the housing 14. For example, the means 42 may include a spring-type locking clip for releasably locking the free end 36 in the locking clip. Such a locking clip may have a generally C-shaped horizontal cross section, and be formed of suitable resilient material, such as spring steel or elastomeric material.

Most preferably, however, the grasping means 42 comprises a generally C-shaped locking collar 48 adapted to engage a corresponding locking ring 50 mounted on the inlet tube 32 generally adjacent the free end 36 of the inlet tube 32, as illustrated in FIG. 4. The locking collar 48 is arcuate having an inner diameter slightly larger than the outer diameter of the rigid portion 46 of the inlet tube 32, and a gap having a width slightly larger than the outer diameter of the rigid main portion 46 of the inlet tube 32. The corresponding locking ring 50 of the inlet tube 32 is generally ring-like, completely encircling the rigid main portion 46 of the inlet tube 32 and having an outer diameter substantially greater than the inner diameter of the locking collar 48. The free end 36 of the inlet tube 32 can be lifted to raise the locking ring 50 away from the locking collar 48 and out of the channel 44 to release the free end 36 of the inlet tube 32 from the holding means 42, and the free end 36 of the inlet tube 32 can be lifted to raise the locking ring 50 over the top of the channel 44 to allow the rigid main portion 46 of the inlet tube 32 to be placed back in the channel 44, with the locking ring 50 engaging the locking collar 48. Most preferably, the resilience of the resiliently-flexible portion 34 of the inlet tube 32 will bias the locking ring 50 downwardly against the locking collar 48 to help hold the free end 36 of the inlet tube 32 in place.

The inlet tube 32 is preferably formed of generally transparent material to allow visual observation of blood flowing in the inlet tube 32. The main portion 46 is preferably formed of generally rigid and transparent material, such as polycarbonate. The rigid main portion 46 extends between the resiliently-flexible portion 34 of the inlet tube 32 and the connector 38.

The resiliently-flexible portion 34 of the inlet tube 32 may be formed of suitable resiliently-flexible medical grade material, for example, polyurethane or polyvinyl chloride (PVC) tubing. The resiliently-flexible portion 34 of the inlet tube 32 is also preferably transparent to allow visual observation of blood flowing in the resiliently-flexible portion 34. A recirculation/prime port 54 may be provided at the "elbow" of the resiliently-flexible portion 34. Most preferably, the resiliently-flexible potion 34 forms a generally U-shaped, fluid trap (FIG. 2) when the inlet tube 32 is in its first position 90 to avoid losing prime when the venous line/tubing 40 is clamped closed. The resiliently-flexible portion 34 may, for example, be solvent bonded to the bottom 18 of the reservoir 10 and the rigid main portion 46 of the inlet tube 32. The resiliently-flexible portion 34 is also preferably formed of kink resistant tubing. See, e.g., U.S. Pat. No. 5,059,375, which is incorporated herein by reference and discloses apparatus and method for producing kink resistant tubing.

A generally opaque, conventional blood defoaming medium 56 is preferably provided within the chamber 22 of the reservoir 10. The blood defoaming medium 56 preferably includes a conventional defoamer. The blood defoaming medium 56 may conveniently be an open cell foam formed into a tubular structure (also 56) extending vertically through the chamber 22 so that any blood entering the reservoir 10 via the inlet tube 32 or cardiotomy inlets (not shown) must pass through the defoaming medium 56 before exiting the reservoir 10. The tubular structure 56 of the defoaming medium 56 defines a kind of blood inlet "antechamber" 58 within the chamber 22 of the housing 14. The inlet tube 32 is in fluid communication with the blood inlet antechamber 58, and the outlet 24 is in fluid communication with the main/outer portion 60 of the chamber 22. As used herein, the term "antechamber" merely means a chamber that the blood from the inlet tube 32 must enter before it can enter the main/outer portion 60 of the chamber 22 of the reservoir 10. Because the defoaming medium is generally opaque, it is difficult to visually observe blood within the antechamber 58. As a result, the ability to visually observe blood flowing in the novel inlet tube 32 is considered advantageous.

An inverted bowl-shaped diverter (not shown) may be provided within the antechamber 58 over the inlet opening 64 to limit spouting of blood flowing in through the inlet opening 64 by directing such blood flow downwardly. Coassigned U.S. Pat. No. 5,403,273 is incorporated herein by reference with respect to this feature, as well as an alternative embodiment in which a generally U-shaped tube would be provided within the antechamber 58 to direct incoming blood generally downwardly into a bowl-shaped fluid trap.

A cardiotomy blood antechamber (not shown) may be provided in the upper portion of the tubular structure 56 of the defoaming medium 56. A conventional blood filtering medium would be provided in the cardiotomy blood antechamber, through which scavenged blood would have to pass before reaching the defoaming medium 56. The filtering medium would be particularly adapted to filter out debris, such as blood clots, before scavenged blood could reach the main/outer portion 60 of the chamber 22. U.S. Pat. Nos. 3,891,416; 3,993,461; 4,208,193; 5,149,318; 5,254,080 and 5,304,164, and coassigned U.S. patent application Ser. No. 08/142,809, filed Oct. 25, 1993, are incorporated herein by reference with respect to their disclosure regarding cardiotomy blood reservoirs and integral venous/cardiotomy blood reservoirs.

Figure 5:
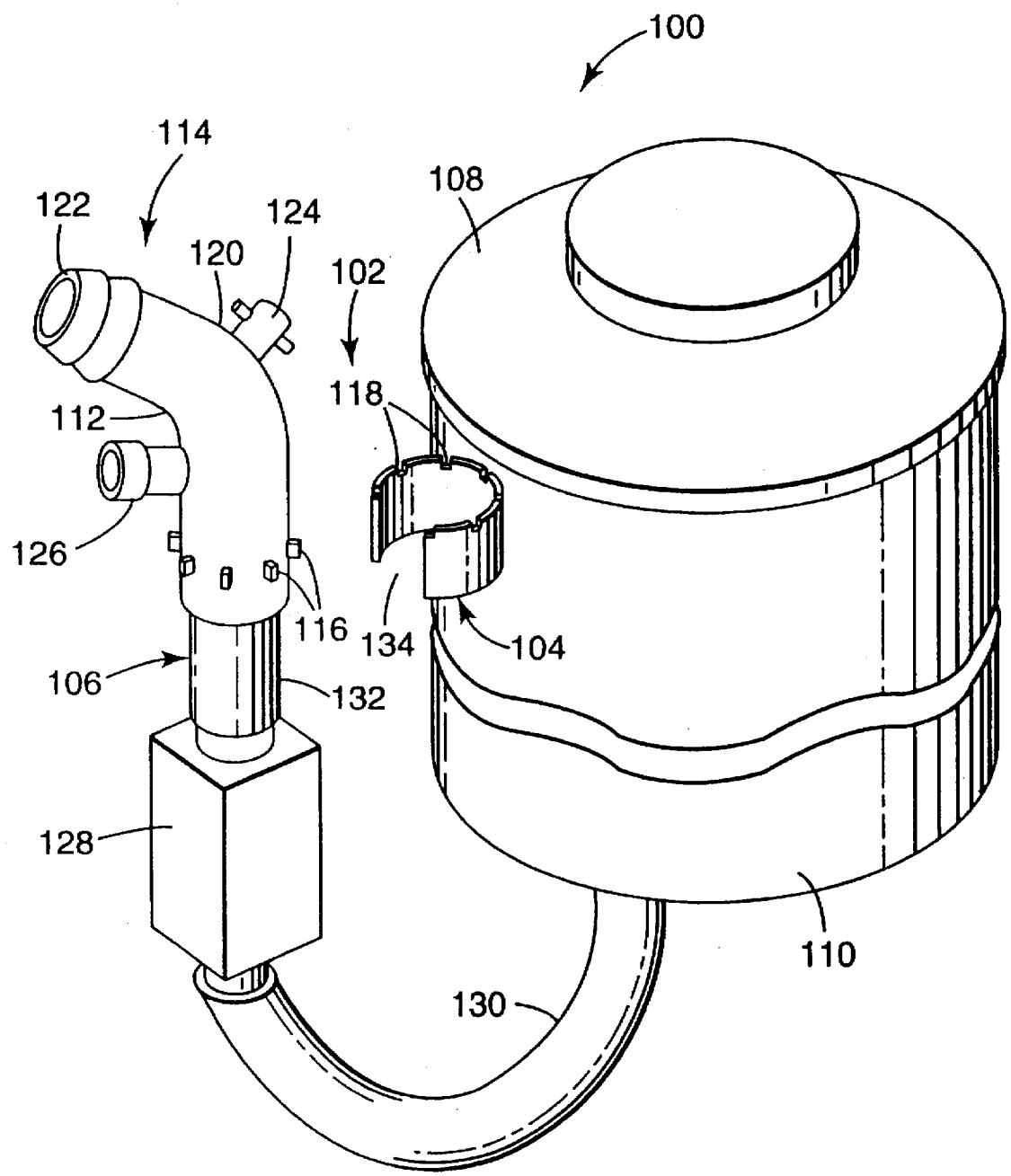
FIG. 5 is a perspective view of a second embodiment of the reservoir of the invention; illustrating a swivel-type indexing connector for holding the free end of the inlet tube.

FIG. 5 illustrates a second embodiment of the blood reservoir, here designated 100, which is similar in many respects to the reservoir 10 of FIGS. 1–4. The holding means 102 of reservoir 100 comprises a split mounting collar 104 for releasably holding the inlet tube 106 generally adjacent the top 108 of the housing 110. A connector 112 is provided on the free end 114 of the inlet tube 106 for connecting tubing in fluid communication with the inlet tube 106.

As illustrated in FIG. 5, the reservoir 100 does not include a channel for receiving the inlet tube 106. This alternative allows the inlet tube 106 to be more readily observed from the side without interference from a U-shaped, channel defining wall.

A plurality of indexing tabs 116 are provided on the connector 112, with the tabs 116 extending radially outwardly from the connector 112. A plurality of indexing notches 118 are formed in the mounting collar 104 for receiving the indexing tabs 116 to radially index the connector 112 of the inlet tube 106 in any of a plurality of radial positions. The connector 112 has a bend 120 formed therein so that the venous inlet port 122 of the connector 112 is offset at an angle from the body of the connector and the longitudinal axis of the free end 114 of the inlet tube 106. The indexing notches 118 and indexing tabs 116 allow the connector 112 to be mounted in different radial positions, in which the venous inlet port 122 faces in different directions. It will be appreciated that the indexing notches 118 and indexing tabs 116 constitute one preferred embodiment of indexing means on the connector 112 of the inlet tube 106 and mounting collar 104 for radially indexing the connector 112 of the inlet tube 106 relative to the mounting collar 104 in a plurality of radial positions.

A temperature probe site 124 and sample port 126 are preferably provided on the connector 112 to allow temperature monitoring of venous blood flowing through the connector 112 and to allow obtaining samples of such venous blood. The sample port 126 may comprise a conventional luer type fitting. The temperature probe site 124 may comprise a conventional stainless steel closed end tube for receiving a conventional temperature probe.

A blood gas monitor 128 may be provided along the inlet tube 106. The blood gas monitor 128 may be of any of the types available under the trade designations "SYSTEM 100", "SYSTEM 300" or "SYSTEM 400" blood gas monitors from Minnesota Mining and Manufacturing Company, St. Paul, Minn. In this regard, coassigned U.S. Pat. Nos. 4,640,820, 4,786,474, 5,289,255 and 5,291,884 are incorporated herein by reference.

The inlet tube 106 may comprise two sections 130 and 132 of resiliently-flexible tubing, extending between the bottom 134 of the blood reservoir 100 and the blood gas monitor 128, and extending between the blood gas monitor 128 and the connector 112. The resiliently-flexible tubing 130 and 132 may be of any suitable resiliently flexible medical grade tubing, for example, polyurethane or polyvinyl chloride (PVC), and is preferably transparent to allow visual observation of blood flowing through the tubing 130 and 132.

The tubing section 132 may have an outer diameter less than the width of the slit 134 in the split collar 104 to facilitate introducing the tubing section 132 into the collar 104 and removing the tubing section 132 from the collar 104. Alternatively, the resiliency of the tubing section 132 and collar 104 may allow the tubing section 132 to be inserted and removed through the slit 134 even if the tubing section 132 has a diameter greater than the width of the slit 134.

It is also contemplated that level sensor mounting pads and liquid level sensors would be provided on the side walls of the reservoirs 10, 100 to provide alerts and/or alarms if, for example, the blood level within the chamber drops below a threshold. A suitable level sensor mounting pad is disclosed in coassigned U.S. patent application Ser. No. 08/420,011, filed Apr. 11, 1995, on Sensor Mounting Pad and Method, which is incorporated herein by reference. Suitable ultrasonic level sensors are available under the trade designations "SARNS™ 8K™" and "SARNS™ 9K™" level sensors from Minnesota Mining and Manufacturing Company, St. Paul, Minn.

Figure 6:
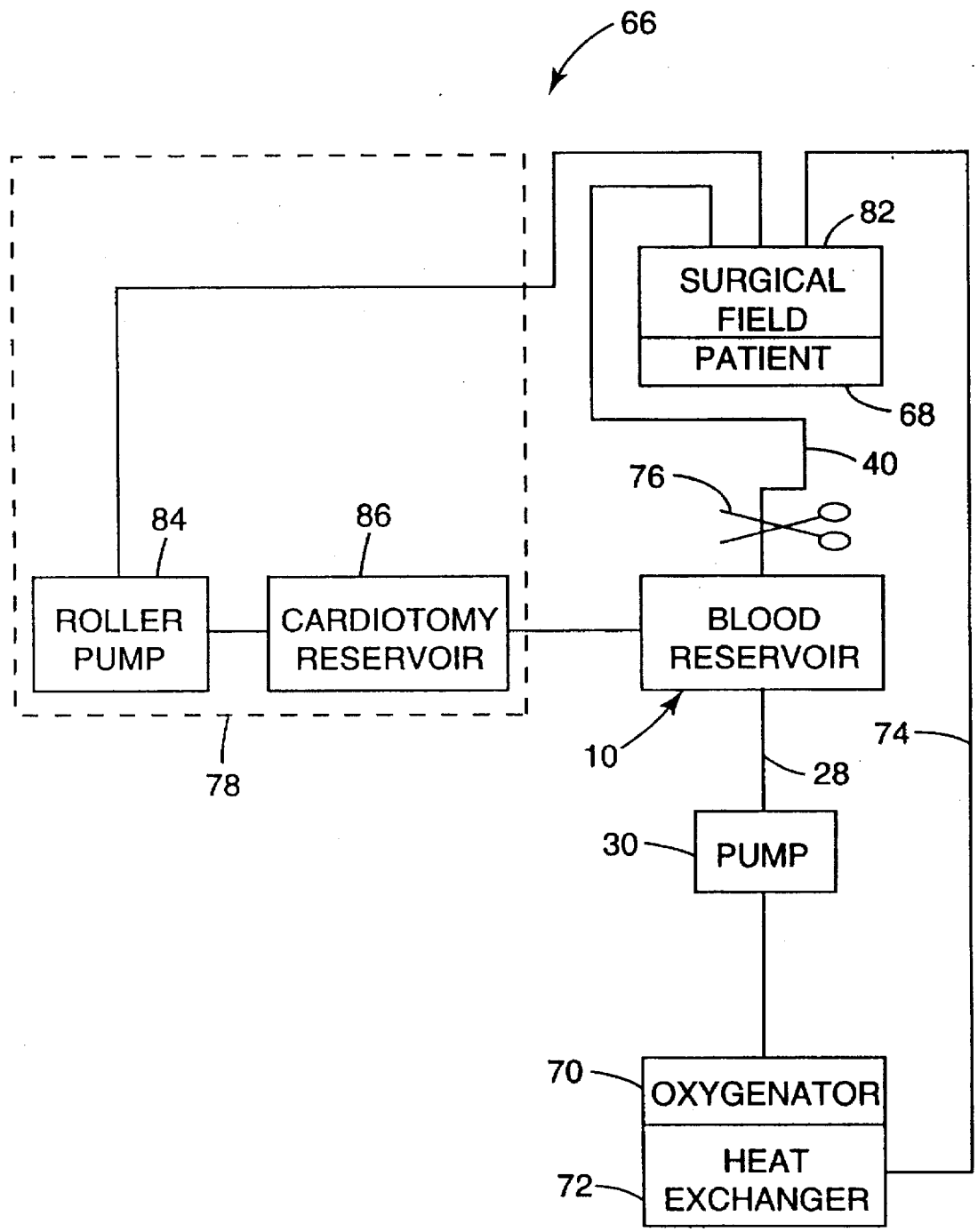
FIG. 6 is a schematic diagram of an extracorporeal circulatory support circuit including either of the blood reservoirs of FIGS. 1–5.

As illustrated in FIG. 6, the reservoir 10 (as well as reservoir 100) is designed to be a component of an extracorporeal circulatory support system 66. The system 66 includes, in addition to the reservoir 10 (or 100), a venous line/tubing 40 for draining blood from the patient 68, with the venous inlet connector 38 (or 112) in fluid communication with the venous line 40; a blood oxygenator 70 and heat exchanger 72 in fluid communication with the outlet 24 of the blood reservoir 10 (or 100) to oxygenate blood before it is returned to the patient 68; a blood pump 30 for pumping blood and prime solution through the system 66; and an arterial line 74 for returning oxygenated blood to the patient 68. A clamp or hemostat 76 is normally provided to clamp the venous line 40.

Most preferably, blood is pumped from the outlet 24 of the reservoir 10 through tubing 28 by a blood pump 30 (e.g., a roller or centrifugal pump) into a blood oxygenator 70 and heat exchanger 72. The blood pump 30 is positioned relative to blood flow through the system 66 between the outlet 24 of the blood reservoir 10 and the inlet of an integral blood oxygenator 70/heat exchanger 72. Suitable roller pumps have been available as part of the systems sold under the trade designation "SARNS™ 9000™" and "SARNS™ 8000™" from Minnesota Mining and Manufacturing Company, St. Paul, Minn. Suitable centrifugal blood pumps are shown in coassigned U.S. Pat. Nos. 4,589,822; 4,606,698; 4,690,002; 4,778,445; 4,781,525 and 4,984,972 (incorporated herein by reference), and have been available under the trade designation "SARNS™ 7850™ Centrifugal Pump" from Minnesota Mining and Manufacturing Company, St. Paul, Minn.

A suitable integral blood oxygenator and heat exchanger 70, 72 has been available under the trade designation "SARNS™ TURBO™" membrane blood oxygenator from Minnesota Mining and Manufacturing Company, St. Paul, Minn. See, also, U.S. Pat. Nos. 3,794,468; 4,690,758; 4,735,775; 5,152,964; 5,255,734 and 5,382,407, and coassigned U.S. patent application Ser. No. 08/142,809, filed Oct. 25, 1993, all of which are incorporated herein by reference.

As illustrated in FIG. 6, the system 66 would normally include a blood scavenging sub-circuit 78. The blood scavenging sub-circuit 78 includes one or more conventional blood suckers (not shown) for sucking blood from the surgical field 82, a roller pump 84 (or other suitable source of vacuum) for applying vacuum to the blood suckers, and alternately cardiotomy reservoir 86 for filtering and defoaming blood scavenged from the surgical field 82. The outlet of the cardiotomy reservoir 86 is in fluid communication with an inlet of the venous blood reservoir 10 (or 100) to supply filtered blood to the venous reservoir 10 (or 100), although it is preferred to have a cardiotomy section integrally provided within the blood reservoir 10 (or 100) as discussed above. Cardiotomy reservoirs are shown in U.S. Pat. Nos. 3,891,416; 3,993,461; 4,208,193 and 4,243,531, which are incorporated herein by reference.

Figure 7:
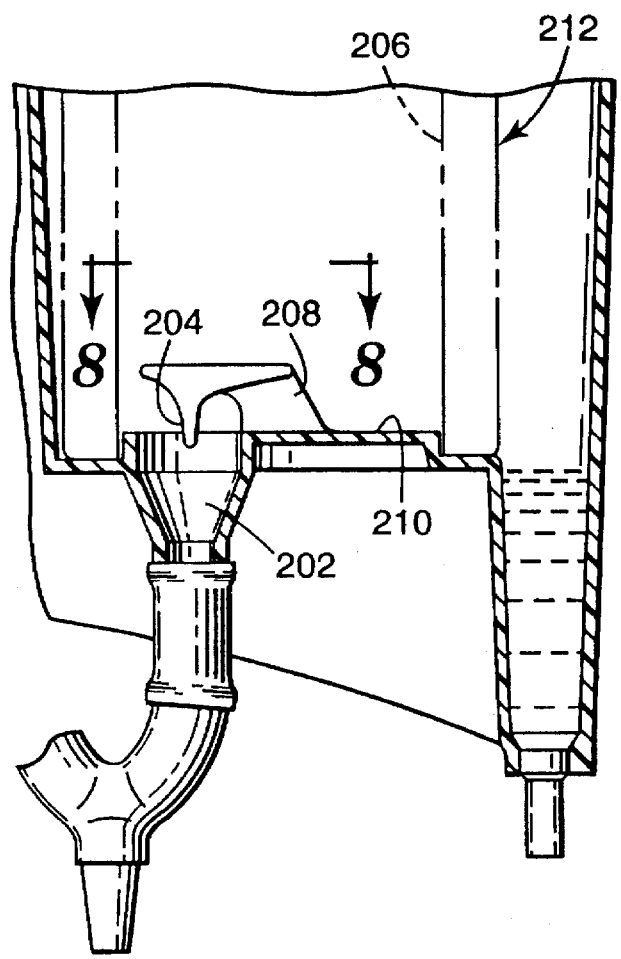
FIG. 7 is a vertical cross sectional view a third embodiment of the reservoir of the invention.
Figure 8:
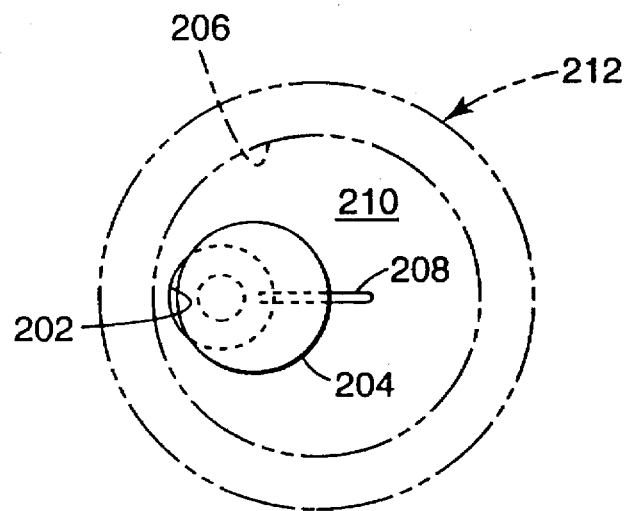
FIG. 8 is a horizontal cross sectional view substantially along line 8—8 of FIG. 7.

FIGS. 7 and 8 illustrate a third embodiment of the reservoir of the invention, here designated 200. The visible venous inlet tube 201 of the reservoir 200 may be similar to either of the inlet tubes 32 or 106 of FIGS. 1–5. The reservoir 200 includes a funnel-shaped venous inlet portion 202, and a diverter cone 204 concentrically arranged over the inlet portion 202 to divert venous blood entering the antechamber 206 of the reservoir 200. Incoming venous blood is relatively gently decelerated in the funnel-shaped venous inlet portion 200 and then deflected by the diverter cone 204, which are believed to reduce hemolysis.

The funnel-shaped venous inlet portion 202 tapers downwardly in the direction away from the antechamber 206 so that the cross section of the funnel-shaped venous inlet portion 202 increases in the direction toward the antechamber 206. The diverter cone 204 tapers downwardly in the generally downward direction toward the funnel-shaped venous inlet portion 202.

The diverter cone 204 is held by a support vane 208 extending upwardly from the floor 210 of the antechamber 206. The support vane 208 is thin, and is radially aligned with respect to the diverter cone 204 and venous inlet 202 to allow blood to readily pass by the support vane 208 with minimum disruption.

The diverter cone and funnel-shaped venous inlet could alternatively be concentric with the tubular defoaming medium 212. In this alternative, three support vanes could be provided to support the diverter cone, with the vanes arranged at equally spaced radial positions relative to the diverter cone. The vanes of this alternative would be radially aligned with respect to the diverter cone and venous inlet. The funnel-shaped venous inlet of this alternative would enter the chamber through the mid-point of the chamber floor.

It will be appreciated that the diverter cone and funnel-shaped venous inlet could also be employed in reservoirs having an otherwise conventional bottom venous inlet arrangement. It will also be appreciated that, while not preferred, a diverter cone could be concentrically arranged over a conventional, non-funnel shaped venous inlet, and a funnel-shaped venous inlet could be used without a diverter cone.

OPERATION

The components of the support system 66 are first connected together as is well known in the art. The patient ends of the arterial line 74 and venous line 40 are connected together, and saline prime solution is added to the blood reservoir 10 through a prime inlet (not shown). The pump 30 is activated to pump the saline prime solution through the various lines 40, 74, oxygenator 70, and heat exchanger 72 to eliminate air from those components. (The system 66 should be closed to air except in the blood reservoir 10 or 100.) Other aspects of the operation of such systems 66, such as the operation of the scavenging sub-circuit 78 and cardioplegia administration, will not be discussed herein.

The blood reservoir 10 or 100 is placed at a lower elevation than the patient 68, with the venous line 40 and arterial line 74 draped from the patient 68. Portions of the venous line 40 may be at a higher elevation than both the patient 68 and the blood reservoir 10. Blood drains from the patient through the venous line 40 due to gravity and relatively low blood pressure within the patient's venous system.

The system 66 is now ready to be connected to the patient 68 to perfuse the saline and blood into the patient 68 in conventional fashion. At some point, the perfusionist will shut the pump 30 down to stop perfusion. The normal practice in many systems of this general type is to clamp the venous line with the hemostat 76 to prevent de-priming of the venous line and inlet tube and migration of air up the inlet tube and venous line. If that practice is not followed and the venous line 40 is not clamped, the fluid trap defined by the generally U-shaped resiliently-flexible portion 34 of the inlet tube 32 or 106 will prevent migration of air up the inlet tube 40 and venous line 74 and de-priming of the inlet tube 32 or 106 and venous line 40 while the pump 30 is not running.

The novel inlet tube 32 (or 106) allows the reservoir 10 (or 100) to be used as a top venous inlet type reservoir or a bottom venous inlet type reservoir. In addition the inlet tube 32 (or 106) may be positioned to allow the reservoir 10 (or 100) to be drained through the inlet tube 32 (or 106). This is accomplished by allowing the resiliently-flexible portion 34 of the inlet tube 32 (or 106) to flex. As illustrated in FIG. 1, this allows the inlet tube 32 (or 106) to be moved between top inlet position 90 (the "first" position); a bottom inlet type position 92 (the "third" or "intermediate" position) and a drain position 94 (the "second" position). In the "first" position 90, the connector 38 is positioned closely proximate the top 16 of the reservoir 10, thus providing a top type inlet. In the "second" position 94, the connector 38 of the inlet tube 32 is positioned at a lower elevation than the bottom 18 of the reservoir 10 to drain the reservoir 10 through the inlet tube 32. The "third" position 92 is intermediate the first and second positions 90 and 94. In the "third" position 92, the inlet tube 32 extends upwardly at an acute angle to the vertical corresponding to the conventional draped position of a venous line connected to a bottom type inlet of a venous blood reservoir.

The transparent nature of the inlet tube 32 (or 106) allows visual observation by and reassurance to the perfusionist. Such visual observation provides ready confirmation that prime has been maintained in the venous inlet, and that blood is flowing into the reservoir 10 or 100 through the inlet tube 32 or 106. In addition, the U-shaped configuration of the resiliently-flexible portion 34 of the inlet tube 32 provides a fluid seal helping to retain prime in the venous line 40 and inlet tube 32, for example, when a hemostat or clamp 76 is used to close the venous line 40 to fluid flow.

The indexing collar 104 and indexing tabs 106 of the reservoir 100 allow the perfusionist to adjust the position of the venous inlet port 122 relative to the top 108 of the reservoir 100 in any of a number of positions. The bend 120 of the connector 112 allows the connector 112 to accommodate the desired direction of approach of the venous line to the top 108 of the reservoir 100.

It will be appreciated that the reservoirs 10 and 100 could have many different shapes, for example, the side walls of the reservoir's housing could have a generally rectangular, round, oblong or elliptical horizontal cross section.

As various changes could be made in the above constructions and methods without departing from the scope of the invention as defined in the claims, it is intended that all matter contained in the above description or shown in the accompanying drawing be interpreted as illustrative and not in a limiting sense.

I claim:

1. A blood reservoir adapted for use in an extracorporeal circulatory support circuit, the blood reservoir comprising:

a housing having top, bottom and side walls defining a chamber inside the housing for holding fluid;

an outlet adjacent the bottom of the housing for draining fluid from the bottom of the chamber, the outlet having a connector for connecting tubing in fluid communication with the outlet;

an inlet tube connected to the housing outside the housing for supplying fluid to the chamber, the inlet tube comprising an elongate tube having a resiliently-flexible portion connecting the inlet tube in fluid communication with the chamber at or adjacent the bottom of the chamber and a free end opposite the resiliently-flexible portion, the free end of the inlet tube having a connector for connecting tubing in fluid communication with the inlet tube; and holding means for releasably holding the inlet tube in a first position, wherein the inlet tube is held in a generally vertical orientation generally adjacent the side wall of the housing, the inlet tube having a length that brings the connector of the inlet tube into generally close proximity with the top of the housing when the holding means holds the inlet tube in its first position, whereby the blood reservoir can be converted between top and bottom inlet configurations.

2. A blood reservoir according to claim 1 wherein the side wall of the housing has a generally vertically extending channel formed therein for releasably receiving the inlet tube.

3. A blood reservoir according to claim 2 wherein the side wall has a channel-forming portion having a generally U-shaped generally horizontal cross section.

4. A blood reservoir according to claim 2 wherein the holding means comprises means for releasably grasping the inlet tube generally adjacent the top of the housing.

5. A blood reservoir according to claim 1 wherein the inlet tube is formed of generally transparent material, the blood reservoir including a generally opaque blood defoaming medium within the chamber of the reservoir, the blood defoaming medium defining a blood inlet antechamber within the housing, the inlet tube being in fluid communication with the blood inlet antechamber.

6. A blood reservoir according to claim 1 wherein the holding means comprises a split mounting collar for releasably holding the inlet tube generally adjacent the top of the housing.

7. A blood reservoir according to claim 6 further comprising indexing means on the connector of the inlet tube and mounting collar for radially indexing the connector of the inlet tube relative to the mounting collar in a plurality of radial positions.

8. A blood reservoir according to claim 7 wherein the indexing means comprises:

a plurality of indexing tabs extending radially outwardly from the connector on the free end of the inlet tube; and a plurality of indexing notches formed in the mounting collar for receiving the indexing tabs to radially index the connector of the inlet tube in any of a plurality of radial positions.

9. A blood reservoir according to claim 1 wherein the inlet tube comprises a main portion extending between the resiliently-flexible portion and the connector, the main portion of the inlet tube being formed of generally rigid material.

10. A blood reservoir according to claim 1 wherein the inlet tube may be moved between its first position to a second position, in which the connector of the inlet tube is positioned at a lower elevation than the bottom of the reservoir to drain the reservoir through the inlet, and to a third position, intermediate the first and second positions, in which the inlet tube extends upwardly at an angle to the vertical.

11. A blood reservoir according to claim 1 further comprising a venous blood inlet portion in fluid communication with the inlet tube and opening through the bottom wall of the chamber of the reservoir, and a diverter cone held concentrically over the venous blood inlet portion and tapering downwardly in the direction toward the inlet portion, the diverter cone diverting blood entering the chamber via the inlet portion generally radially outwardly.

12. A blood reservoir according to claim 11 wherein the venous blood inlet portion is generally funnel-shaped to decelerate venous blood flowing in the inlet portion before the blood enters the chamber of the reservoir.

13. A system according to claim 11 wherein the holding means comprises a split mounting collar for releasably holding the inlet tube generally adjacent the top of the housing, and indexing means on the connector of the inlet tube and mounting collar for radially indexing the connector of the inlet tube relative to the mounting collar in a plurality of radial positions.

14. A system according to claim 13 wherein the indexing means comprises:

a plurality of indexing tabs extending radially outwardly from the connector on the free end of the inlet tube; and a plurality of indexing notches formed in the mounting collar for receiving the indexing tabs to radially index the connector of the inlet tube in any of a plurality of radial positions.

15. A blood reservoir according to claim 11 wherein the venous blood inlet portion comprises a generally funnel-shaped inlet portion to decelerate venous blood flowing in the inlet portion before the blood enters the antechamber of the reservoir.

16. A blood reservoir according to claim 15 further comprising a mounting vane extending upwardly from the bottom wall of the housing into the antechamber for holding the diverter cone in concentric position over the inlet opening, the mounting vane being radially aligned with respect to the diverter cone.

17. An extracorporeal circulatory support system for supporting a patient during heart bypass surgery, the system comprising:

a venous line for draining blood from the patient;

blood reservoir comprising:

a housing having top, bottom and side walls defining a chamber inside the housing for holding fluid;

an outlet adjacent the bottom of the housing for draining fluid from the bottom of the chamber, the outlet having a connector for connecting tubing in fluid communication with the outlet;

an inlet tube connected to the housing outside the housing for supplying fluid to the chamber, the inlet tube comprising an elongate tube having a resiliently-flexible portion connecting the inlet tube in fluid communication with the chamber at or adjacent the bottom of the chamber and a free end opposite the resiliently-flexible portion, the free end of the inlet tube having a connector for connecting the venous line in fluid communication with the inlet tube; and holding means for releasably holding the inlet tube in a first position, wherein the inlet tube is held in a generally vertical orientation generally adjacent the side wall of the housing, the inlet tube having a length that brings the connector of the inlet tube into generally close proximity with the top of the housing when the holding means holds the inlet tube in its first position, whereby the blood reservoir can be converted between top and bottom inlet configurations;

a blood oxygenator in fluid communication with the outlet of the blood reservoir to oxygenate blood before it is returned to the patient;

a pump for pumping blood through the system; and an arterial line for returning oxygenated blood to the patient.

18. A system according to claim 17 wherein the side wall of the housing of the blood reservoir has a generally vertically extending channel formed therein for releasably receiving the inlet tube, the side wall having a channel-forming portion having a generally U-shaped generally horizontal cross section, the holding means comprising means in the channel for releasably grasping the inlet tube generally adjacent the top of the housing.

19. A system according to claim 17 wherein the inlet tube of the blood reservoir is formed of generally transparent material; the blood reservoir including a generally opaque blood defoaming medium within the chamber of the reservoir, the blood defoaming medium defining a blood inlet antechamber within the housing, the inlet tube being in fluid communication with the blood inlet antechamber; the inlet tube comprising a main portion extending between the resiliently-flexible portion and the connector, the main portion of the inlet tube being formed of generally rigid material; the inlet tube being movable between its first position to a second position, in which the connector of the inlet tube is positioned at a lower elevation than the bottom of the reservoir to drain the reservoir through the inlet, and to a third position, intermediate the first and second positions, in which the inlet tube extends upwardly at an angle to the vertical.

* * * * *

UNITED STATES PATENT AND TRADEMARK OFFICE
CERTIFICATE OF CORRECTION

PATENT NO. : 5,667,485
DATED : September 16, 1997
INVENTOR(S) : Erin J. Lindsay

It is certified that error appears in the above-indentified patent and that said Letters Patent is hereby corrected as shown below:

Figure 2, "56" should read --58--.

Figure 2, "58" should read --56--.

Figure 7, add numeral --201--.

Col. 5, line 43, after "5,254,080" insert --;--.

Col. 5, line 44, "and" (first occurrence) should be deleted.

Col. 5, lines 44-45, delete "coassigned U.S. patent application Serial No. 08/142,809, filed October 25, 1993" and insert --5,514,335--.

Col. 11, line 20, "opening" should read --portion--.

Signed and Sealed this

Eleventh Day of July, 2000

Attest:

Q. TODD DICKINSON

Attesting Officer                Director of Patents and Trademarks